United States Patent [19]

Manzer et al.

[11] Patent Number: 5,243,108

[45] Date of Patent: Sep. 7, 1993

[54] ALUMINUM FLUORIDE CATALYST COMPOSITIONS AND USE THEREOF IN A CHLOROFLUORINATION PROCESS FOR PREPARING 1,1-DICHLORO-1,2,2,2-TETRAFLUOROETHANE

[75] Inventors: Leo E. Manzer, Wilmington; Frederick N. Tebbe, Hockessin, both of Del.

[73] Assignee: E. I. du Pont de Nemours and Company, Wilmington, Del.

[21] Appl. No.: 865,807

[22] Filed: Apr. 7, 1992

Related U.S. Application Data

[63] Continuation of Ser. No. 700,191, Jun. 3, 1991.

[51] Int. Cl.$^5$ .............................................. C07C 17/08
[52] U.S. Cl. .................................................... 570/166
[58] Field of Search ........................................ 570/166

[56] References Cited

U.S. PATENT DOCUMENTS

| | | |
|---|---|---|
| 2,748,177 | 5/1956 | Miller et al. . |
| 2,755,313 | 7/1956 | Calfee et al. ............... 570/166 |
| 3,314,749 | 4/1967 | Fukui et al. . |
| 3,650,987 | 3/1972 | Vecchio et al. . |
| 3,720,722 | 3/1973 | Wada et al. ............... 570/166 |
| 4,605,798 | 8/1986 | Abel et al. . |
| 4,766,260 | 8/1988 | Manzer et al. . |
| 4,902,838 | 2/1990 | Manzer et al. . |
| 5,008,475 | 4/1991 | Manzer et al. . |

FOREIGN PATENT DOCUMENTS 1578933  11/1980  United Kingdom .

OTHER PUBLICATIONS

F. N. Tebbe, *J. Am. Ceram. Soc.*, 71 [4] pp. 204-206 (1988).
Chemical Abstracts 74:55778t (1991).
Vecchio et al., *J. Fluorine Chem.*, 4, pp. 117-139 (1974).

*Primary Examiner*—Alan Siegel

[57] ABSTRACT

A catalyst composition is disclosed which consists essentially of an aluminum fluoride prepared by the reaction of aluminum hydroxide and HF. Also disclosed is a process for preparing 1,1,-dichloro-1,2,2,2-tetrafluoroethane by chlorofluorination which comprises the step of contacting a gaseous mixture comprising at least one tetrahaloethylene having the formula $C_2Cl_{4-x}F_x$ wherein x is an integer from zero to 3 and both $Cl_2$ and HF with said catalyst composition at an elevated temperature; and a process for producing 2-chloro-1,1,1,2-tetrafluoroethane and/or 1,1,1,2-tetrafluoroethane by hydrodechlorinating 1,1-dichloro-1,2,2,2-tetrafluoroethane prepared by said chlorofluorination.

4 Claims, No Drawings

ALUMINUM FLUORIDE CATALYST COMPOSITIONS AND USE THEREOF IN A CHLOROFLUORINATION PROCESS FOR PREPARING 1,1-DICHLORO-1,2,2,2-TETRAFLUOROETHANE

This application is a continuation of application Ser. No. 07/700,191 filed Jun. 3, 1991 now abandoned.

FIELD OF THE INVENTION

This invention relates to catalysts and their use for the manufacture of 1,1-dichloro-1,2,2,2-tetrafluoroethane (i.e. "CFC-114a"), and more particularly to aluminum fluoride catalysts and use thereof for preparing CFC-114a.

BACKGROUND OF THE INVENTION

Fluorinated aluminas are well known as fluorination or chlorofluorination catalysts. For example the use of both aluminum fluoride and nickel for fluorination or chlorofluorination reactions is described in U.S. Pat. No. 3,650,987. The fluorided alumina is often prepared by the addition of HF to $Al_2O_3$. The products from these reactions contain large Amounts of the symmetrical isomers of various chlorofluorocarbons. The addition of metal dopants increases the amount of symmetrical isomers.

German (DDR) Patent Specification 117,580 discloses a process for the preparation of asymmetrical fluorochlorocarbon compounds of the $C_2$ series (e.g. CFC-114a) by the reaction of tetrachloroethylene, chlorine and hydrogen fluoride over a metal doped aluminum fluoride catalyst. In the example of this patent with the highest amount of asymmetrical products, the 1,1-dichloro-1,2,2,2-tetrafluoroethane (CFC-114a)/1,2-dichloro-1,1,2,2-tetra-fluoroethane (CFC-114) ratio is about 11.5; and the 1,1,1-trichloro-2,2,2-trifluoroethane (CFC-113a)/1,1,2-trichloro-1,2,2-trifluoroethane (CFC-113) ratio is about 8.0. However 57.4% of the product is chloropentafluoroethane (CFC-115), which is generally considered an undesirable byproduct in CFC-114a manufacturing processes. In another example where 6.1% of the product is CFC-115, the ratios of CFC-114a/CFC-114 and CFC-113a/CFC-113 are 7.3 and 3.8 respectively.

European Patent Application 317,981 discloses a process for isomerizing CFC-113 to CFC-113a followed by fluorination with HF to produce CFC-114a. In the example of this patent with the highest ratio of CFC-114a/CFC-114 (52.7) the ratio of CFC-113a/CFC-113 is 1.1. In other examples the CFC-114a/CFC-114 ratio varied from 45.3 to 5.5 and the CFC-113a/CFC-113 ratio from 6.2 to 1.1.

Japanese Kokai 1-172347 discloses a process for the preparation of CFC-114a by first disproportionating CFC-114 to CFC-113a followed by reaction with HF. In the examples the CFC-114a/CFC-114 ratios vary from 9.0 to 16.7 and the CFC-113a/CFC-113 ratios from 0.1 to >36. In the high 113a/113 ratio example the yield of 114a is only 15.0%. In the other examples the yields of 114a varied from 43.0% to 51.0%.

It is also known in the art (GB 1,578,933) that both $CClF_2CClF_2$ (CFC-114) and $CF_3CCl_2F$ (CFC-114a) may be hydrogenated over a Pd catalyst to $CHF_2CHF_2$ (HFC-134) and $CF_3CH_2F$ (HFC-134a) respectively. The latter compound (HFC-134a) is considered a refrigerant suitable for replacing $CCl_2F_2$ since it does not significantly contribute to stratospheric ozone depletion while $CCl_2F_2$ is suspected of being a major contributor.

Accordingly, there is continued interest in developing economic and efficient processes for preparing 1,1-dichloro-1,2,2,2-tetrafluoroethane.

SUMMARY OF THE INVENTION

In accordance with this invention, a process is provided for preparing 1,1-dichloro-1,2,2,2-tetrafluoroethane by chlorofluorination. The process comprises the step of contacting a gaseous mixture comprising at least one tetrahaloethylene having the formula $C_2CCl_{4-x}F_x$, wherein x is an integer from zero to 3, and both $Cl_2$ and HF with a catalyst composition at an elevated temperature, said catalyst composition consisting essentially of an aluminum fluoride prepared by the reaction of aluminum hydroxide and HF. The 1,1-dichloro-1,2,2,2-tetrafluoroethane prepared by the process may be hydrodechlorinated to produce 2-chloro-1,1,1,2-tetrafluoroethane and/or tetrafluoroethane. A catalyst composition is also provided in accordance with this invention which consists essentially of an aluminum fluoride prepared by the reaction of aluminum hydroxide with HF.

DETAILED DESCRIPTION OF THE INVENTION

A process for preparing 1,1-dichloro-1,2,2,2-tetrafluoroethane by chlorofluorination is provided in accordance with this invention and comprises the step of contacting a gaseous mixture comprising at least one tetrahaloethylene and both $Cl_2$ and HF with a catalyst composition at an elevated temperature, said catalyst composition consisting essentially of an aluminum fluoride prepared by the reaction of aluminum hydroxide and HF. Tetrahaloethylenes useful in this invention include those having the formula $C_2Cl_{4-x}F_x$, wherein x is an integer from zero to 3. Examples of tetrahaloethylenes useful for this process include $CCl_2=CCl_2$, $CClF=CCl_2$, $CClF=CClF$, $CF_2=CCl_2$, and $CF_2=CClF$, and mixtures of these. Tetrachloroethylene is preferred.

The reaction of the tetrahaloethylene with HF and $Cl_2$ is the presence of the catalyst composition of the instant invention is conducted at an elevated temperature. Suitable temperatures are generally within the range of about 300° C. to 450° C. Preferably the temperature is within the range of about 300° C. to 400° C., and most preferably is within the range of about 350° C. to 375° C. Contact times can influence the yield of the reaction to some extent. Preferably the temperature and contact time are balanced to achieve a yield of at least about 95% total of CFC-114a and recyclable by-products (i.e. by-products having less than 5 fluorine atoms per molecule); and preferably the aluminum fluoride purity of the catalyst composition is sufficient to provide a molar ratio of 1,1-dichloro-1,2,2,2-tetrafluoroethane to 1,2-dichloro-1,1,2,2-tetrafluoroethanes (i.e. of CFC-114a to CFC-114) of at least about 45 and most preferably sufficient to provide a molar ratio of CFC-114a to CFC-114 of at least about 47.5. A contact time within the range of about 5 to 100 seconds is typical. Preferably the contact time is within the range of about 10 to 90 seconds, and most preferably is within the range of about 15 to 60 seconds.

The HF in the gaseous mixture is preferably at least the stoichiometric amount needed to produce CFC-114a. The molar ratio of the HF to the tetrahaloethylene is typically within the range of about 1:1 to 20:1.

Preferably the ratio of HF to the tetrahaloethylene is within the range of about 3:1 to 10:1, and most preferably is within the range of about 4:1 to 7:1.

Preferably $Cl_2$ is provided in the gaseous mixture in at least the amount needed to produce CFC-114a. The molar ratio of $Cl_2$ to the tetrahaloethylene is preferably within the range of about 1:1 to 2:1, and most preferably is about 1:1.

The desired product of the present invention can be separated by a usual method such as fractional distillation. By-products having less than five fluorine atoms per molecule such as $C_2Cl_5F$, $C_2Cl_4F_2$, $C_2F_3Cl_3$, and $CClF_2CClF_2$ are considered recyclable, and may advantageously be further contacted with the catalyst composition used in this invention.

The reaction of the tetrahaloethylene with HF and chlorine may be conducted in any suitable reactor, including fixed and fluidized bed reactors which are charged with the catalyst compositions. The reaction vessel should be constructed from materials which are resistant to the corrosive effects of HF and $Cl_2$ such as Hastelloy ® nickel alloy and Inconel ® nickel alloy. Optionally, before the catalyst is contacted by the tetrahaloethylenes, it may be pretreated with gaseous HF.

Pressure is not critical. Atmospheric and superatmospheric pressures are the most convenient and are therefore preferred.

1,1-dichloro-1,2,2,2-tetrafluoroethane produced by this invention has utility as a solvent and as an intermediate for the preparation of 2-chloro-1,1,1,2-tetrafluoroethane and/or 1,1,1,2-tetrafluoroethane. Indeed an improved process for producing 1,1,1,2-tetrafluoroethane and/or 2-chloro-1,1,2,2-tetrafluoroethane by hydrodechlorinating 1,1-dichloro-1,2,2,2-tetrafluoroethane is provided in accordance with this invention. The improvement comprises the step of preparing CFC-114a by chlorofluorination using tetrahaloethylenes and the catalyst compositions of this invention as described above.

Catalyst compositions are provided in accordance with this invention which consist essentially of an aluminum fluoride prepared by the reaction of aluminum hydroxide with HF.

The catalyst composition of this invention may be suitably prepared by reacting aqueous HF (e.g. 48% solution) with aluminum hydroxide. Suitable aluminum hydroxide may be prepared by the hydrolysis of $AlR_3$, where each R is independently selected from $C_1$ to $C_6$ alkyl groups. For example, a preparation of high purity $Al(OH)_3$ prepared by the hydrolysis of $Al(CH_2CH_3)_3$ is described by F. N. Tebbe et al., *J. Am. Ceram. Soc.*, 71 [4], C-204–C-206, (1988). Suitable aluminum hydroxide may also be prepared by hydrolysis of $Al(OR)_3$, where each R is independently selected from $C_1$ to $C_6$ alkyl groups. For example, high purity $Al(OH)_3$ may be prepared by the hydrolysis of $Al(OCH(CH_3)CH_2CH_3)_3$.

A particularly useful catalyst composition consisting essentially of an aluminum fluoride is prepared by dissolving aluminum hydroxide in aqueous HF; evaporating the resulting solution to obtain a residue of an aluminum fluoride; and heating said residue to produce a dried solid. The catalyst compositions of this invention are also useful for catalyzing other reactions such as the chlorofluorination of $CF_3CCl_3$, $CF_3CHClF$ and/or $CF_3CH_3$ to CFC-114a, isomerization of $CClF_2$—$CClF_2$ to $CCl_2F$—$CF_3$, isomerization of $CHF_2$—$CHF_2$ to $CH_2F$-$CF_3$, fluorination of $CF_3$—$CHCl_2$ to $CF_3$—$CHClF$ and fluorination of $CHCl$=$CCl_2$ to $CClF_2CH_2Cl$ and $CF_3CH_2Cl$.

Practice of the invention will become further apparent from the following non-limiting examples.

EXAMPLE I

Aluminum sec-butoxide (Alfa, 95%), about 300 g, was placed in an open dish and allowed to hydrolyze in air over two days. The aluminum hydroxide produced was a powder and clusters of powdery solids. In a polyethylene tray a portion of the aluminum hydroxide (39 g) was dissolved in 48% aqueous hydrofluoric acid (100 mL). The volatiles were evaporated at ambient temperature over three days in a fume hood. The resulting white residue was dried at 100° C. for 48 hours. The solid was then heated in air at a rate of 5° C./min to 500° C., and held at this temperature for three hours. After cooling, the solid (30.3 g) was crushed and passed through a sieve to yield fines (12.8 g) and a fraction of granules 12×20 mesh in size (17.5 g). Analysis showed 31.5% Al and 227 ppm (0.0227%) of metal ion impurities.

EXAMPLE II

A reactor (a 0.5 inch ID, 12 inch long Inconel ® nickel alloy pipe) was charged with the aluminum fluoride catalyst composition (15.7 g, 25 mL) prepared as described in Example I above. The charged reactor was placed in a sand bath. The bath was gradually heated to 250° C. while nitrogen gas at a flow rate of 50 cc/minute was passed through the reactor to remove traces of water. HF and nitrogen gas (1:4 molar ratio) were then passed through the reactor. An exotherm of about 10° C., which travelled down the reactor, was observed. The temperature was gradually raised to 450° C., the nitrogen flow decreased with time until neat HF was passed through the reactor. The HF flow was stopped after no further exotherm was recorded. $HF/CCl_2$=$CCl_2/Cl_2$ in a 5/1/1 molar ratio was then passed over the catalyst at 375° C. and a 30 second contact time. The reactor effluent was sampled on-line with a Hewlett-Packard 5890 gas chromatograph using a 20 foot long, ⅛" diameter, column containing Krytox ® perfluorinated polyether on an inert support and a helium flow of 35 cc/minute. Gas chromatographic conditions were 70° C. for 3 minutes followed by temperature programming to 180° C. at a rate of 6° C./minute. Analysis showed the following to be present (area percent): 25.4% $CCl_2$=$CCl_2$, 0.2% $CCl_3CCl_2F$, 0.5% $CCl_2FCCl_2F/CClF_2CCl_3$, 1.6% $CCl_2FCClF_2$ (CFC-113), 9.4% $CF_3CCl_3$ (CFC-113a), 1.2% $CClF_2CClF_2$ (CFC-114), 58.5% $CF_3CCl_2F$ (CFC-114a), 1.0% $CClF_2CF_3$ (CFC-115), 0.1% $CClF_2CHCl_2$, and 0.2% $CCl_2$=$CClF$.

The yield to useful products including both CFC-114a and recyclable by-products, is greater than 98% and the molar ratio of CFC-114a/CFC-114 is 49.

Particular embodiments of the invention are described in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. An improved process for producing 2-chloro-1,1,1,2-tetrafluoroethane and/or 1,1,1,2-tetrafluoroethane by hydrodechlorinating 1,1-dichloro-1,2,2,2-tetrafluoroethane, the improvement comprising the step of preparing said 1,1-dichloro-1,2,2,2-tetrafluoroethane by contacting a gaseous mixture comprising at least one tetrahaloethylene having the formula $C_2C_{4-x}F_x$, wherein x is an integer from zero to 3, and both $Cl_2$ and HF at a temperature within the range of about 300° C. to 450° C., with a catalyst composition consisting essentially of an aluminum fluoride (i) prepared by the reaction of HF and aluminum hydroxide and (ii) having sufficient purity to provide a product wherein the molar ratio of 1,1-dichloro-1,2,2,2-tetrafluoroethane to 1,2-dichloro-1,1,2,2-tetrafluoroethane is 45:1.

2. The improved process of claim 1 wherein said aluminum hydroxide is prepared by the hydrolysis of $AlR_3$ or the hydrolysis of $Al(OR)_3$ where each R is selected from $C_1$ to $C_6$ alkyl groups.

3. The improved process of claim 2 wherein the aluminum fluoride has 0.0227 weight percent of metal ion impurities.

4. The improved process of claim 1 wherein the aluminum fluoride has 0.0227 weight percent of metal ion impurities.

* * * * *